United States Patent
Burgard

(10) Patent No.: US 6,759,544 B2
(45) Date of Patent: *Jul. 6, 2004

(54) ANTIMICROBIALLY ACTIVE ACESULFAME COMPLEXES, PROCESS FOR THEIR PREPARATION AND THEIR USE

(75) Inventor: Andreas Burgard, Frankfurt am Main (DE)

(73) Assignee: Nutrinova Nutrition Specialties & Food Ingredients GmbH, Wiesbaden (DE)

(*) Notice: Subject to any disclaimer, the term of this patent is extended or adjusted under 35 U.S.C. 154(b) by 12 days.

This patent is subject to a terminal disclaimer.

(21) Appl. No.: 10/165,398

(22) Filed: Jun. 7, 2002

(65) Prior Publication Data

US 2003/0023084 A1 Jan. 30, 2003

(30) Foreign Application Priority Data

Jun. 22, 2001 (DE) ......................................... 101 30 298

(51) Int. Cl.$^7$ ............... C07F 3/06; C07F 1/08; C07F 1/10; A61K 31/28; A61K 31/295

(52) U.S. Cl. ............ 556/119; 556/111; 544/2; 544/3; 514/492; 514/499; 514/501; 514/502

(58) Field of Search ............... 556/111, 119; 544/2, 3; 514/492, 499, 501, 502

(56) References Cited

U.S. PATENT DOCUMENTS

| | | | |
|---|---|---|---|
| 4,332,791 A | 6/1982 | Raaf et al. ............ 424/52 |
| 4,374,122 A | 2/1983 | Stroz et al. | |
| 4,595,629 A | 6/1986 | Mays | |
| 4,607,100 A | 8/1986 | Clauss et al. | |
| 4,652,444 A | 3/1987 | Maurer ............ 424/49 |
| 4,832,994 A | 5/1989 | Fey ............ 428/48 |
| 5,011,982 A | 4/1991 | Clauss et al. | |
| 5,032,612 A | 7/1991 | Smolko et al. ......... 514/495 |
| 5,037,634 A | 8/1991 | Williams et al. ........... 424/49 |
| 5,103,046 A | 4/1992 | Clauss et al. | |
| 5,122,366 A | 6/1992 | Shubair ............ 424/49 |
| 5,366,636 A | 11/1994 | Marchin et al. .......... 210/665 |
| 5,389,360 A | 2/1995 | Mobley et al. ............ 424/49 |
| 5,688,492 A | 11/1997 | Galley et al. | |
| 6,139,864 A | 10/2000 | Durr et al. | |
| 6,517,862 B2 * | 2/2003 | Burgard ............ 424/439 |
| 2001/0041738 A1 | 11/2001 | Burgard | |

FOREIGN PATENT DOCUMENTS

| | | | | |
|---|---|---|---|---|
| DE | 32 11 258 A1 | 10/1982 | | |
| DE | 34 37 090 A1 | 5/1986 | ............ | A61K/6/00 |
| DE | 693 24 679 T2 | 3/1995 | | |
| DE | 100 13 259 A1 | 9/2001 | | |
| EP | 0 155 634 A2 | 9/1985 | | |
| EP | 0 399 479 A1 | 11/1990 | ............ | A61K/9/68 |
| EP | 1 134 223 A2 | 9/2001 | ............ | C07F/1/00 |
| GB | 2348370 A | 10/2000 | ............ | A61K/7/16 |
| WO | WO 95/01156 A1 | 1/1995 | ............ | A61K/7/16 |
| WO | WO 96/01231 A1 | 1/1996 | ............ | C02F/1/50 |
| WO | WO 97/38586 A1 | 10/1997 | ............ | A23B/4/20 |
| WO | WO 97/40812 A1 | 11/1997 | ............ | A61K/7/16 |
| WO | WO 99/55342 A1 | 11/1999 | ............ | A61K/31/70 |
| WO | WO 00/00166 A2 | 1/2000 | ............ | A61K/7/16 |
| WO | WO 00/44338 A1 | 8/2000 | ............ | A61K/7/16 |
| WO | WO 00/51559 A1 | 9/2000 | ............ | A61K/7/16 |
| WO | WO 00/62738 A1 | 10/2000 | ............ | A61K/7/00 |

OTHER PUBLICATIONS

P. D. Marsh, *J. Clin. Periodontal, Dentifrices Containing New Agents For The Control Of Plaque And Gingivitis: Microbiological Aspects* (1991), 18(6) pp. 462–467.

Watson, G.K.; Cummins, D.; Van der Ouderaa, F.J.G. *Caries Res. Inhibitiion Of Acid Production By Streptoccus Mutans Nctc 10449 By Zinc And The Effect Of Metal Speciation* (1991), 25(6), pp. 431–437.

Arens, Max; Travis, Sharon, *J. Clin. Microbiol Zinc Salts Inactivate Clinical Isolates of Herpes Simplex Virus in Vitro* (2000), 38(5), 1758–1762.

K. Yamamoto et al. *Dent. mater. Antibacterial Activity Of Silver Ions Implanted In Sio$_2$ Filler On Oral Streptococci* (1996), 12(4), pp. 227–229.

Z. Ernährungswiss *Acesulfame K, Cyclamate And Saccharin Inhibit The Anaerobic Fermentation Of Glucose By Intestinal Bacteria* (1985), 24, pp. 231–235.

W. Beck; E. Ambach; U. Nagel *Chemische Berichte, Palladium–und Platin (II)–Komplexe mit den Anionen von 6–Methyl–1,2,3–oxathiazin–4(3H)–on–2,2–dioxid und N–2–Pyrimidinylsulfanilamid* 118, No. 2, (1985), pp. 444–449.

* cited by examiner

Primary Examiner—Porfirio Nazario-Gonzalez
(74) Attorney, Agent, or Firm—ProPat, L.L.C.

(57) ABSTRACT

Complex compounds containing acesulfame have good antimicrobial action, in particular antibacterial action, and are distinguished by the fact that they are complex compounds of metallic elements such as zinc, copper, silver, or nonmetallic quaternary ammonium cations, such as the cetylpyridinium cation, with acesulfame. The invention also relates to a process for preparing the compounds and their use in the oral hygiene sector.

12 Claims, No Drawings

US 6,759,544 B2

ANTIMICROBIALLY ACTIVE ACESULFAME COMPLEXES, PROCESS FOR THEIR PREPARATION AND THEIR USE

BACKGROUND OF THE INVENTION

The present invention relates to complex compounds containing acesulfame which have an antimicrobial action, in particular an antibacterial action.

Various metal cations, for example zinc(II), copper(II) and silver(I) ions, and also quaternary ammonium cations, for example the cetylpyridinium cation, have antimicrobial action and are therefore used to eliminate or reduce unwanted microorganisms, for example bacteria and viruses, in foods and feeds. Antimicrobially active cations are also frequently used in oral care compositions and pharmaceuticals against bacteria and viruses which lead to infections, for example stomatitis, laryngitis, herpes or caries, in the oral and pharyngeal cavities.

Zinc(II) ions are described in WO 97/40812 and WO 00/00166 as active compounds against halitosis, dental plaque, dental tartar and infections in the oral area. It is known that zinc(II) salts inhibit proteolysis by direct action on the proteases of the bacteria. These are cysteine and methionine proteases which can cause halitosis by release of sulfur compounds (Marsh, P D, J. Clin. Peridontal 18 (6) 462-467,1991). WO 00/62738 describes a lipstick to combat halitosis which comprises zinc(II) citrate as antibacterial active compound.

Zinc(II) ions are known to show their antibacterial activity in particular against those bacteria which cause caries, for example Streptococcus mutans (see Watson, G. K.; Cummins, D.; Van der Ouderaa, F. J. G. Caries Res. (1991), 25(6), 431-7). Colgate PerioGard® Pluse toothpaste contains, for example, zinc(II) citrate as active compound against caries.

The antiviral activity of zinc(II) ions against *Herpes simplex* and rhinoviruses has been described in many publications and patents (for example Arens, Max; Travis, Sharon, J. Clin. Microbiol. (2000), 38(5), 1758-1762; WO 99/55342).

Copper(II) ions, owing to their antibacterial action, in particular in oral hygiene, are used in the form of citrates, bisglycinates or bicarbonates (see U.S. Pat. Nos. 4,332,791, 4,652,444, 5,037,634 and 5,389,360).

Silver(I) ions are occasionally used for preparing and sterilizing drinking water in small amounts which are sufficient to obtain permanent sterilization and long-term maintenance of freshness of the water owing to the bactericidal action of the silver compounds (see WO 96/01231, U.S. Pat. No. 5,366,636).

K. Yamamoto et al. (Dent. Mater. (1996), 12(4), 227–229) report the antibacterial activity of silver(I) ions which are implanted in silicate fillings against streptococci occurring in the mouth.

Silver(I) ions are also used in mouthwashes for withdrawal from the smoking habit (see U.S. Pat. No. 5,032,612). During smoking, in the presence of silver(I) ions nicotine forms nicotinamide which causes an unpleasant taste in the mouth, so that an aversion to cigarette smoke is said to be formed (U.S. Pat. No. 5,122,366). Silver(I) acetate, incorporated into tablets for sucking, is also said to be suitable for successful therapies for withdrawal from smoking (see U.S. Pat. No. 4,832,994).

Cetylpyridinium cations have, as quaternary ammonium compounds, an antibacterial action and are used in particular in mouthwashes (see WO 00/51559, WO 00/44338). EP-A-0 399 479 and GB-A 2348370 describe a chewing gum for oral and pharyngeal disinfection in which cetylpyridinium cations form the antibacterially active constituent. WO 97/38586 reports a method which is said to achieve inhibition or elimination of bacteria in contaminated foods by means of quaternary ammonium compounds. This method uses quaternary ammonium compounds, in particular cetylpyridinium chloride, which, in foods, eliminates microorganisms, for example staphylococci, listeria, salmonellae, *Escherichia coli* bacteria and fungi such as *Aspergillus flavus*. The quaternary ammonium compounds are applied in dissolved form by spraying onto foods such as meat, fish, vegetables and fruit.

Furthermore, cetylpyridinium cations are used in numerous pharmaceutical preparations, for example in ®Hextrilettes from Warner Lambert, ®Dobendan from Boots Healthcare and ®Frubienzym from Boehringer Ingelheim Pharma KG as tablets for sucking in the case of infections of the oral, neck and throat cavity which are caused by viruses and bacteria. Cetylpyridinium chloride accumulates on the cell walls of the pathogens, destroys them and kills the germs.

Colgate PerioGard Plus® oral rinse also comprises cetylpyridinium chloride in active amounts.

Synergistic combinations of zinc(II) salts and cetylpyridinium chloride against halitosis are also described in WO 00/51559.

The focus of the present invention is in the field of use of antibacterial cations, in particular in the oral hygiene sector. The widespread disease caries which is caused by bacteria, for example *Streptococcus mutans*, can be restricted by antibacterially active cations. Halitosis is caused in many cases by bacteria which decompose food residues present in the mouth and release sulfur compounds. Elderly people and diabetes patients frequently complain of xerostomia, which is caused by a decreased production of saliva in the mouth. Xerostomia is an ideal growth medium for bacteria, so that infections, halitosis and caries are observed significantly precisely in the case of diabetes. Food residues and bacteria can no longer be washed away in xerostomia due to the lack of saliva. The consequence is that the bacteria in the mouth can multiply better on the rich supply of nutrient media. In order that pathogens and their consequences, for example caries or halitosis, can be reduced or eliminated, antimicrobially active cations are used in toothpaste, chewing gums and mouthwashes.

However, it is a problem that many salts of the above-described antimicrobially active cations, even in small amounts, taste unpleasant, and in particular, have an astringent taste. The incorporation of compounds of these antibacterially active cations into foods, dental care compositions, drugs or feeds and supplying them via special preparations is therefore a difficult undertaking on account of the lack of acceptance by humans and animals.

An object of the present invention was thus to provide a form which tastes as pleasant as possible of antimicrobial, in particular antibacterial, active compounds with which the acceptance and possibilities of targeted employment of the active compounds in foods, dental care compositions, drugs and feeds can be significantly improved.

BRIEF DESCRIPTIONS OF THE INVENTION

Surprisingly, it has been found that the known sweetener acesulfame (6-methyl-3,4-dihydro-1,2,3-oxathiazin-4-one 2,2-dioxide), which has previously only been offered as potassium salt (acesulfame-K), but of which, salts with alkali metals and alkaline earth metals, for example sodium, potassium, magnesium and calcium salts, the acidic acesulfame itself, which is called acesulfamic acid, and some amine salts are also known, forms stable complexes with these antimicrobially active, in particular antibacterially active, cations containing the acesulfame anion. These complexes are distinguished surprisingly by a pleasantly sweet taste which is not associated with the astringent note of many salts of the antibacterially active cations.

The present invention thus achieves the object via complex compounds of metallic elements such as zinc, copper, silver, or nonmetallic quaternary ammonium cations, for example the cetylpyridinium cation, with acesulfame.

DETAILED DESCRIPTION OF THE INVENTION

According to the invention these are preferably complexes of acesulfame which are composed of a metal or of a quaternary ammonium ion and one or two acesulfame molecules and which, in addition, may contain water of crystallization. The inventive complexes are stoichiometrically defined compounds in which the metal or the quaternary ammonium ion is present as cation and the acesulfame molecule is present as anion.

The inventive compounds are stable and do not decompose even on incorporation into chewing gum or other antimicrobially active preparations. They also have the advantage that they do not separate as salts, which would lead to inhomogeneities of taste. Such separations are a known problem in food and drug manufacture.

In particular, the inventive complexes can be used in intermediates or precursors without the antimicrobially active cation and the acesulfame separating. They may therefore be incorporated without problem in the preparations with which they are to be consumed, for example chewing gum, chewing tablets, compressed tablets or other preparations for oral application.

As a result of the fact that the metal cations or the quaternary ammonium cation is preferably ionically bound in these complexes, they are, after solvolysis by water, immediately antimicrobially active. Using the present invention, the antimicrobial activity of these acesulfame complexes is shown in comparison to salt compounds otherwise used, such as zinc(II) sulfate, copper(II) sulfate, silver(I) nitrate and cetylpyridinium chloride, by the antibacterial potency toward bacteria such as *Streptococcus mutans* (ATCC 25175), *Actinomyces odontolyticus* (ATCC 17982) and *Staphylococcus aureus* (ATCC 6538) by way of example by determining the minimum inhibitory concentration. The antibacterial activity toward other bacteria and the antiviral properties of these acesulfame complexes are not limited by the examples and can be applied to other bacteria and viruses.

Method for Determining the Minimum Inhibitory Concentration

The samples, to determine the minimum inhibitory concentration, are dissolved in WSH (water of standardized hardness) and mixed with twice-concentrated Caso-Bouillon pH 5.5. After inoculation with the test organisms, the solutions of the test organisms *Streptococcus mutans* (ATCC 25175) and *Actinomyces odontolyticus* (ATCC 17982) were overlayered with paraffin and incubated for a period of three days at a temperature of 37° C.

The solution of the test organism *Staphylococcus aureus* (ATCC 6538) was incubated for two days at 37° C. The samples were then streaked onto Caso agar and incubated for two days at 37° C.

| | Microorganisms | | |
|---|---|---|---|
| Substrate | *Streptococcus mutans* (ATCC 25175) | *Actinomyces odontolyticus* (ATCC 17982) | *Staphylococcus aureus* (ATCC 6538) |
| | Minimum inhibitory concentration | | |
| $Zn(acesulfame)_2 \cdot 2H_2O$ | 23.73 mmol/l | 11.8 mmol/l | 23.73 mmol/l |
| $ZnSO_4 \cdot 7H_2O$ | 17.5 mmol/l | 17.5 mmol/l | 17.5 mmol/l |
| $Cu(acesulfame)_2 \cdot 3H_2O$ | 2.26 mmol/l | 11.37 mmol/l | 11.37 mmol/l |
| $CuSO_4 \cdot 5H_2O$ | 4.01 mmol/l | 20.13 mmol/l | 20.13 mmol/l |
| $Ag(acesulfame) \cdot 0.25H_2O$ | 18.31 mmol/l | 18.31 mmol/l | 3.65 mmol/l |
| $AgNO_3$ | 5.91 mmol/l | 5.91 mmol/l | 5.91 mmol/l |
| Cetylpyridinium(acesulfame) | 2.14 μmol/l | 2.14 μmol/l | 107.03 μmol/l |
| Cetylpridinium chloride·$H_2O$ | 2.79 μmol/l | 2.79 μmol/l | 139.66 μmol/l |

The minimum inhibitory concentration values from the above table show that the respective acesulfame complexes display their antibacterial activity at the same order of magnitude as the respective simple inorganic salts. In most cases, the antibacterial activity of the acesulfame complexes is even better, that is to say the minimum inhibitory concentration is lower than with the corresponding inorganic salt, for example in the case of the cetylpyridinium compounds. The better antibacterial activity of the cetylpyridinium-acesulfame compared with cetylpyridinium chloride can be explained by earlier observations that sweeteners, including acesulfame-K have an inhibitory action against bacteria.

DE-A 34 37 090 describes the inhibitory action on dental caries by inhibiting sugar metabolism of oral bacteria such as *Streptococcus mutans* by acesulfame-K, and its combination with other sweeteners such as saccharin and cyclamate. DE-A 32 11 258 also reports on a process for treating teeth to suppress or prevent caries in which the teeth are brought into contact with acesulfame-K in a sufficient amount to inhibit the growth of *Streptococcus mutans* strains in the oral cavity or on the teeth. However, the amounts of acesulfame-K necessary for an effective suppression of caries lead to complete oversweetening which is no longer acceptable in terms of taste.

M. Pfeffer et al. report on inhibition of glucose fermentation in *Streptococcus mutans* bacteria in the presence of the sweeteners acesulfame-K, cyclamate and saccharin (see Z. Ernährungswiss. 24, 1985, 231–235). The interpretation of the experiments of M. Pfeffer et al. leads, in the context of cellular physiology, to the suggestion that the sweeteners act on glucose transport systems in the bacterial cytomembrane.

In the case of silver nitrate, the greater antibacterial effect compared with silver-acesulfame complexes is probably explained by the additional antibacterial property of the nitrate anion.

The inventive novel acesulfame complexes can be used without problem in the customary processing steps for foods and in drugs and cosmetics, for example dental care compositions and oral care compositions, or in feeds, for example in the form of a premix. Processing is simple and is performed by known methods. In the case of solid preparations, the inventive complexes are mixed in solid form, if appropriate in a suitable particle size, with the other ingredients. For use in tablets, compressed compositions and comparable products and pulverulent preparations, they can be granulated with other ingredients suitable therefor and further processed as granules. Owing to their good solubility, however, they can also be readily used in liquid products from said sectors or processed in the form of their aqueous solutions.

Finally, the present invention also relates to a process for preparing the inventive complexes. The acesulfame or its potassium salt, acesulfame-K, serving as starting substance are commercially available, or can be prepared, as can any other acesulfame salts, by the process described in EP-A 0 155 634.

To prepare the inventive complexes a process is employed using which other ionic constituents of the starting materials suitable for preparation may be removed. This can be achieved either by separating off slightly soluble compounds of the other ionic constituents or by using starting materials for which, from the start, only the antimicrobially active cations and acesulfame remain in a solution from which the complexes are isolated in a suitable manner. These processes include reacting acesulfame salts whose cations form suitable slightly soluble compounds which may be precipitated out, in particular the calcium salt but also the barium salt of acesulfame, with soluble salts of the above-described cations whose anions form slightly soluble compounds with the cations of the acesulfame salt, for example sulfates, or reacting basic carbonates of the antimicrobially active cations with acesulfamic acid (acesulfame) with release of $CO_2$.

In each case precipitates formed are if appropriate separated off before the desired acesulfame complexes are isolated. They are preferably isolated by crystallization, for example by evaporating the solvent, preferably water or water-miscible solvents, or by adding water-miscible solvents to the reaction mixture. Preferred water-miscible solvents are, for example, alcohols.

The acesulfame salts serving as starting materials of the reaction can be introduced, for example, as aqueous solution, or else can be formed in a "one-pot" reaction from acesulfame and a suitable alkaline earth metal carbonate (Ba, Ca salt) before addition of the salt containing the antimicrobially acting cation.

The invention is described in more detail by the following examples without being restricted in its scope as a result.

EXAMPLE 1

Acesulfame-Zinc Complex

Method 1:

20 mmol (3.947 g) of slightly soluble barium carbonate (or 20 mmol of calcium carbonate) were introduced in 20 ml of water and 40 mmol (6.525 g) of acesulfame-H were added. After completion of $CO_2$ formation, a homogeneous solution was formed, from which slightly soluble barium sulfate (or calcium sulfate) was precipitated out using 20 mmol (0.575 g) of zinc(II) sulfate heptahydrate. After filtering off the precipitate and concentrating the solution, the acesulfame-zinc complex crystallized in the form of colorless crystals at 97% yield.

Method 2:

10 mmol (3.42 g) of slightly soluble basic zinc carbonate hydrate ($ZnCO_3.2Zn(OH)_2.H_2O$) were introduced in 20 ml of water and 60 mmol (9.789 g) of acesulfame-H were added. After completion of $CO_2$ formation, a homogeneous solution was formed. The acesulfame-zinc complex crystallized out in the form of colorless crystals at 99% yield after concentration of the solution.

Method 3:

20 mmol (1.31 g) of metallic zinc powder were introduced in 20 ml of water and 40 mmol (6.525 g) of acesulfame-H were added. After completion of $H_2$ formation, a homogeneous solution resulted. The acesulfame-zinc complex crystallized out in the form of colorless crystals at 99% yield after concentration of the solution.

The acesulfame-zinc complex decomposes at 255° C.

The crystal structure of the acesulfame-zinc complex was established by X-ray structural analysis.

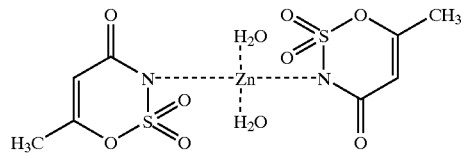

$(Ace)_2Zn$, $2C_4H_4NO_4S.Zn.2H_2O$, $M_r=425.69$, monoclinic, C2/c, a=12.907(4), b=5.584(2), c=21.222(8) Å, β=91.31(3)°, V=1529.2(8) Å$^3$, Z=4, $D_x$=1.849 Mg m$^{-3}$, λ (Mo—Kα)=0.71073 Å, $\mu$=1.932 mm$^{-1}$, F(000)=864, T=293 (2) K, R=0.0235 and $R_w$=0.0649 for I>2σ(I) (1356 reflections), R=0.0255 and $R_w$=0.0669 for all 1436 unique CCD data. $S(F_o^2-F_c^2)^2$ was minimized.

EXAMPLE 2

Acesulfame-Copper Complex

Method 1:

20 mmol (3.947 g) of slightly soluble barium carbonate (or 20 mmol of calcium carbonate) were introduced in 20 ml of water and 40 mmol (6.525 g) of acesulfame-H were added. After completion of $CO_2$ formation a homogeneous solution resulted, from which slightly soluble barium sulfate (or calcium sulfate) was precipitated using 20 mmol (0.499 g) of copper(II) sulfate pentahydrate. After filtering off the precipitate and concentrating the solution, the acesulfame-copper complex crystallized out in the form of blue crystals at 96% yield.

Method 2:

10 mmol (2.21 g) of slightly soluble basic copper carbonate ($CuCO_3.Cu(OH)_2$) were introduced in 20 ml of water and 40 mmol (6.526 g) of acesulfame-H were added. After completion of $CO_2$ formation, a homogeneous blue solution resulted. After concentration of the solution, the acesulfame-copper complex crystallized out in the form of blue crystals at 98% yield.

The blue acesulfame-copper complex decolorizes at 117° C. and decomposes at 179° C.

The crystal structure of the acesulfame-copper complex was established by X-ray structural analysis.

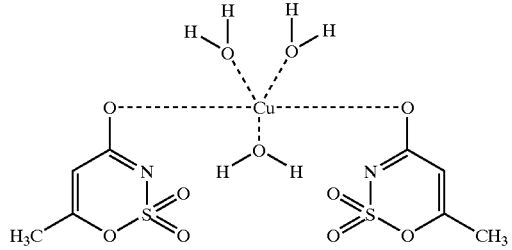

$(Ace)_2Cu$, $2C_4H_4NO_4S \cdot Cu \cdot 3H_2O$, $M_r=441.87$, monoclinic, C2/c, a=19.30(2), b=9.677(9), c=9.007(8) Å, β=102.92(2)°, V=1640(3) Å$^3$, Z=4, $D_x$=1.790 Mg m$^{-3}$, λ (Mo—Kα)=0.71073 Å, μ=1.645 mm$^{-1}$, F(000)=900, T=293 (2) K, R=0.0371 and $R_w$=0.0753 for I>2σ(I) (1251 reflections), R=0.0440 and $R_w$=0.0791 for all 1448 unique CCD data. $S(F_o^2-F_c^2)^2$ was minimized.

EXAMPLE 3

Acesulfame-Silver Complex

Method 1:

A solution of 30 mmol (5.148 g) of silver(I) nitrate in 30 ml of water was added to a solution of 30 mmol (6.037 g) of acesulfame-K in 30 ml of water. After addition was complete, the colorless precipitate formed was filtered off by suction and washed twice, each time with 10 ml of water. 88% of colorless acesulfame-silver crystals resulted. The reaction and subsequent workup as described above need not be carried out in the absence of light.

Method 2:

15 mmol (3.48 g) of slightly soluble silver(I) oxide were introduced in 30 ml of water and a solution of 30 mmol (4.895 g) of acesulfame-H in 30 ml of water was added. After the reaction was complete, and workup as in method 1, 80% of colorless acesulfame-silver crystals resulted.

The crystal structure of the acesulfame-silver complex was established by X-ray structural analysis.

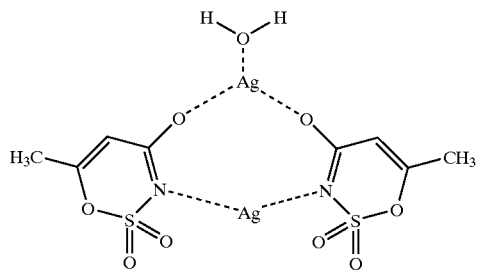

Crystal Data:

crystal system: monoclinic space group: P2/n; Z=8 empirical formula: $C_4H_8AgNO_4S \cdot 0.25H_2O$ cell dimensions: a=13.438(3) Å
   b=7.525(2) Å
   c=15.067(3) Å
   β=113.111(3)° cell volume: 1401.3(5) Å$^3$ temperature: 293 (2) K calculated density: 2.602 Mg/m$^3$ unique reflections: 2584 model quality: $R_{obs.data}$=2.15%

EXAMPLE 4

Acesulfame-Cetylpyridinium Complex

Method 1:

10 mmol (3.653 g) of cetylpyridinium chloride.H$_2$O were dissolved in 25 ml of methanol and suspended with 10 mmol (2.012 g) of acesulfame-K. After stirring for 1.5 hours at room temperature, the precipitate formed was filtered off. The filtrate was concentrated in vacuo. The oily residue then crystallized out. This produced 90% of colorless nonhygroscopic crystals.

Method 2:

10 mmol (3.653 g) of cetylpyridinium chloride.H$_2$O were suspended in 75 ml of methylene chloride and 10 mmol (2.012 g) of acesulfame-K were added. After stirring for 1.5 hours at room temperature the precipitate formed was filtered off. The filtrate was concentrated in vacuo. The oily residue then crystallized out. This produced 95% of colorless nonhygroscopic crystals.

60-MHz-$^1$H-NMR (CDCl$_3$): δ(ppm)=0.9 (t, 3H, CH$_3$-cetylpyridine), 1.25 (m, 28H, CH$_2$-cetylpyridine), 2.05 (s, 3H, CH$_3$-acesulfame), 4.95 (t, 2H, CH$_2$-N-cetylpyridine), 5.6 (s, 1H, CH-acesulfame), 8.5 (m, 3H, CH-aromatic-cetylpyridine), 9.6 (d, 2H, CH-aromatic-cetylpyridine).

What is claimed is:

1. A complex compound which contains acesulfame and has antimicrobial action, which is a complex compound of metallic element, or a nonmetallic quaternary ammonium cation, with acesulfame.

2. A complex compound as claimed in claim 1, wherein it is a complex of acesulfame which is composed of a metal or a quaternary ammonium ion and one or two acesulfame molecules and while, in addition, contains or does not contain water of crystallization.

3. A complex compound as claimed in claim 1, wherein it is a stoichiometrically defined compound in which the metal or the quaternary ammonium ion is present as cation and the acesulfame molecule is present as anion.

4. A complex compound as claimed in claim 1, wherein the antimicrobial action is an antibacterial action.

5. A complex compound as claimed in claim 1, wherein the metallic element is zinc, copper or silver.

6. A complex compound as claimed in claim 1, wherein the quaternary ammonium cation is a cetylpyridinium cation.

7. A process for preparing complex compounds as claimed in claim 1 in which the individual constituents of the complex compounds are reacted in a solvent in such a manner that other ionic constituents of the starting materials suitable for the preparation can be removed by separating off slightly soluble compounds of the other ionic constituents or in which only those starting materials are used in the case of which after the reaction is complete only the antimicrobial active cation and acesulfame remain in solution, the complex compounds then being isolated in a suitable manner.

8. The process as claimed in claim 7, wherein acesulfame salts, are reacted with suits whose anion forms a slightly soluble compound with the cation of the acesulfame salt.

9. The process as claimed in claim 7, wherein basic carbonates of antimicrobially active cations are reacted with acesulfamic acid with release of CO$_2$.

10. The process as claimed in claim 8, wherein precipitates formed are separated off before the acesulfame complexes are isolated.

11. The process as claimed in claim 7, wherein the complex compounds are isolated by crystallization.

12. The process as claimed in claim 7, wherein the solvent is water or a water-miscible organic solvent.

* * * * *